United States Patent [19]

Rhodes

[11] 4,172,138
[45] Oct. 23, 1979

[54] METHOD AND COMPOSITION OF MATTER FOR THE TREATMENT OF DRY COWS FOR MASTITIS

[76] Inventor: Russell E. Rhodes, 1 Sheraton La., Norwich, Conn. 06360

[21] Appl. No.: 780,408

[22] Filed: Mar. 23, 1977

[51] Int. Cl.² ............................................ A61K 31/43
[52] U.S. Cl. .................................................... 424/271
[58] Field of Search ........................................ 424/271

[56] References Cited
PUBLICATIONS

Dowrick et al.–Chem. Abst., vol. 82 (1975), p. 144, 980k.
Ziv et al.–Chem. Abst., vol. 80 (1974), p. 128, 182e.
Schmid et al.–Veterinary Bulletin, vol. 43 (1973), p. 314, Item 2470.
Jacobs et al.–Veterinary Bulletin, vol. 42 (1972), p. 735, Item 6552.
Lindt–Veterinary Bulletin, vol. 46 (1976), p. 703, Item 5284.

*Primary Examiner*—Sam Rosen
*Attorney, Agent, or Firm*—Murray & Whisenhunt

[57] ABSTRACT

Dry cows are treated for mastitis by infusion into the udder of the cow a dosage of a limited solubility penicillin salt in a slow release base, with an antibiotic in the form of neomycin added in an alternate embodiment.

6 Claims, No Drawings ically 4,172,138

METHOD AND COMPOSITION OF MATTER FOR THE TREATMENT OF DRY COWS FOR MASTITIS

BACKGROUND OF THE INVENTION

The present invention relates to a method of treating dry cows for mastitis as well as to a composition of matter particularly suited for such treatment. More particularly, the present invention relates to the use of a limited solubility penicillin salt, preferably in a slow release base, for the treatment of cows for mastitis during the dry or non-milking period. In addition, an antibiotic neomycin may be added to the composition to overcome mastitis causing bacteria which are resistant to the action of penicillin.

In the treatment of cows during the dry or non-milking period to overcome bovine mastitis the use of high solubility penicillin salts and complementary antibiotics have heretofore been applied in dosages of high concentration. For example, such a treatment product would contain 1,000,000 units of procaine penicillin G and 1,000 milligrams of dihydrostreptomycin. Such high dosage units have the obvious disadvantage of high cost and, in some cases, the desired residual effects of the procaine penicillin G remain in the udder of a treated cow for only a few days. As a result, it is necessary to repeat dosages at short intervals in order to maintain a sufficiently high residual procaine penicillin G level in the animal being treated. The practice of retreatment in dry cows is impractical and undesirable. It is impractical because the cow is usually put out to pasture during the dry period and, therefore, not easily accessible for treatment and it is undesirable because retreatment breaks the teat seal which forms naturally during the dry period to protect the udder from invasion by bacteria.

It is an object of the present invention to provide a composition of matter which is particularly suited for the treatment of cows for bovine mastitis during their dry period. It is also an object to provide a composition of matter wherein the product has a penicillin salt of limited solubility in a slow release base so that the effectiveness of the penicillin is prolonged over an extended period of time. It is still a further object to incorporate into the composition of matter neomycin and/or other antibiotics to treat other bacteria, such as *Escherichia coli, Aerobacter aerogenes, Klebsiella sp.*, and some strains of *Staphylococcus aureus* bacteria which are insensitive or resistant to penicillin.

SUMMARY OF THE INVENTION

The present invention provides a composition of matter containing a limited solubility penicillin (i.e., one having a solubility in water of less than about 2 mg./ml.) which has been put into a slow release base, preferably a base formed from a vegetable oil and about 0.5 to 10 percent of a suitable gelling agent, such as aluminum monostearate, castor wax, bees wax or a similar suitable gelling agent, with a preferred range of about 2 to 7.5 percent. The vegetable oils may be peanut oil, sesame oil or other suitable and similar oils.

DESCRIPTION OF A SPECIFIC EMBODIMENT

A preferred example of the composition made in accordance with the present invention is given by way of illustration.

EXAMPLE 1

A composition for treating dry cows for mastitis was prepared as follows:

| | |
|---|---|
| Benzathine penicillin G | 500,000 u |
| Neomycin sulfate equivalent to Neomycin base | 500 mg. |
| 6% Aluminum Monostearate in Peanut oil       base qs. | 10 ml. |

The benzathine penicillin G (N, N dibenzyl ethylene diamine di benzyl penicillinate) has a molecular weight of about 909, a potency of 1,307 u/mg., and a solubility in water of 0.5 mg./ml. A cow which was treated with a dosage of 500,000 units of the composition of Example 1 was found to have a residual of benzathine penicillin G in u/ml. as follows:

| Days Past Treatment | Residual Benzathine Penicillin G (u/ml.) In The Udder |
|---|---|
| 8 | 5.37 |
| 10 | 3.67 |
| 12 | 4 |
| 16 | 3.57 |
| 23 | 2.2 |
| 30 | 0.11 |

On the other hand a cow which was also given a dosage of 500,000 u of procaine penicillin G was found to have the following residual procaine penicillin G after treatment:

| Days Past Treatment | Residual Procaine Penicillin G (u/ml.) In The Udder |
|---|---|
| 8 | 7.68 |
| 10 | 1.56 |
| 12 | .21 |
| 16 | less than 0.01 (not detectable) |
| 23 | less than 0.01 (not detectable) |
| 30 | less than 0.01 (not detectable) |

From the above it is clear the amount of the low solubility benzathine penicillin G which remained for effectively treating mastitis was substantially greater than that which remained for the procaine penicillin over the extended 30 day treatment. While the initial amount of the procaine penicillin remaining at the 8th day was higher, it rapidly dissipated and by the tenth day it was less than half of that of the remaining benzathine penicillin G.

Another limited solubility penicillin salt which may be used is benethamine penicillin G (N benzyl phenethylamine benzyl penicillinate). It may be prepared as a composition of matter in accordance with the following example:

EXAMPLE 2

| | |
|---|---|
| Benethamine penicillin G | 500,000 u |
| Neomycin sulfate equivalent to Neomycin base | 600 mg |
| 6% Aluminum monostearate in Peanut oil       qs. | 10 ml |

Other examples of compositions in accordance with the present invention including those in which a procaine penicillin G may be added, if desired, for the initial high concentration treatment because of its greater solubility are as follows:

EXAMPLE 3

| | |
|---|---|
| Benzathine penicillin G | 750,000 u |
| Neomycin sulfate equivalent to Neomycin base | 500 mg |
| 2.5% Thixcin R in | |
| Peanut oil    base qs. | 10 ml |

EXAMPLE 4

| | |
|---|---|
| Benzathine penicillin G | 250,000 u |
| Procaine penicillin G | 250,000 u |
| Neomycin sulfate equivalent to Meomycin base | 250 mg |
| 6% Aluminum monostearate in | |
| Sesame oil    base gs. | 20 ml |

EXAMPLE 5

| | |
|---|---|
| Benzathine penicillin G | 500,000 u |
| Procaine penicillin | 250,000 u |
| Neomycin sulfate equivalent to Neomycin base | 350 mg |
| 2.5% Thixcin R in | |
| Sesame oil    base qs. | 20 ml |

To those skilled in the art other examples of limited solubility penicillins will be evident as will be other antibiotics in place of the neomycin.

What is claimed:

1. A method for the treatment of dry cows for bovine mastitis for an extended period of time comprising the step of infusing into the udder of the dry cow an effective amount of a composition containing a penicillin salt having a water solubility of less than 2 mg/ml and selected from a group consisting of benzathine penicilline G and benethamine penicillin G in a slow release base containing a vegetable oil and a gelling amount of a gelling agent.

2. A method as defined in claim 1 wherein an antibiotic in the form of neomycin is included in the composition.

3. A method as defined in claim 2 wherein the amount of gelling agent present in the vegetable oil is from 0.5 to 10% by weight.

4. A composition for sustained treatment of dry cows for bovine mastitis by infusion of the composition into the udder of the dry cow, comprising an effective amount of a penicillin salt having a water solubility of less than 2 mg/ml and selected from a group consisting of benzathine penicillin G and benethamine penicillin G in a slow release base containing a vegetable oil and a gelling amount of a gelling agent.

5. A composition of matter as defined in claim 4 wherein an antibiotic in the form of neomycin is contained therein.

6. A composition of matter as defined in claim 5 wherein the amount of gelling agent present in the vegetable oil is from 0.5 to 10% by weight.

* * * * *